United States Patent
Schiffer

[19]

[11] Patent Number: 5,963,294
[45] Date of Patent: Oct. 5, 1999

[54] METHOD FOR USING THERAPEUTIC GLASSES FOR STIMULATING A CHANGE IN THE PSYCHOLOGICAL STATE OF A SUBJECT

[76] Inventor: Fredric Schiffer, 72 Sheridan Rd., Wellesley, Mass. 02181

[21] Appl. No.: 08/857,291

[22] Filed: May 16, 1997

[51] Int. Cl.[6] ................................................. G02C 7/16
[52] U.S. Cl. ............................................. 351/46; 351/45
[58] Field of Search .............................. 351/45, 46, 49, 351/47, 48, 44, 57, 41, 158, 246, 247

[56] References Cited

U.S. PATENT DOCUMENTS

| Re. 16,862 | 1/1928 | Moran | 351/49 |
|---|---|---|---|
| 1,752,889 | 4/1930 | Cornwell | 351/49 |
| 3,111,675 | 11/1963 | Mora | 2/14 |
| 3,421,233 | 1/1969 | Gaal | 35/35 |
| 3,838,913 | 10/1974 | Schwarz | 351/47 |
| 4,498,743 | 2/1985 | Feinbloom | 351/45 |
| 4,698,022 | 10/1987 | Gilson | 434/36 |
| 4,715,702 | 12/1987 | Dillon | 351/44 |
| 4,828,380 | 5/1989 | Cherian | 351/45 |
| 4,938,582 | 7/1990 | Leslie | 351/158 |
| 4,943,152 | 7/1990 | Whelen | 351/49 |
| 5,050,982 | 9/1991 | Meissner | 351/203 |
| 5,083,858 | 1/1992 | Girerd | 351/44 |
| 5,264,877 | 11/1993 | Hussey | 351/45 |
| 5,321,441 | 6/1994 | Osterlund | 351/44 |
| 5,372,504 | 12/1994 | Buechler | 434/35 |
| 5,424,786 | 6/1995 | McCarthy | 351/46 |
| 5,440,359 | 8/1995 | Bloch-Malem | 351/203 |
| 5,452,027 | 9/1995 | Tylec | 351/46 |
| 5,488,438 | 1/1996 | Cochran | 351/45 |
| 5,570,144 | 10/1996 | Lofgren-Nisser | 351/247 |

FOREIGN PATENT DOCUMENTS 2 666 991  9/1990  France .
WO 93/08784  5/1993  WIPO .

OTHER PUBLICATIONS

Levick, S.E., et al., "Asymmetrical Visual Deprivation: A Technique to Differentially Influence Lateral Hemispheric Function," *Perceptual and Motor Skills*, 76:1363–1382 (1993).

Schiffer, F., "Cognitive Activity of the Right Hemisphere: Possible Contributions to Psychological Function," *Harvard Rev. Psychiatry*, 4 (3): 126–138 (1996).

Fouty, H.E, et al., "A Novel Contact–Lens System to Assess Visual Hemispheric Asymmetries," *Perceptual and Motor Skills*, 74:567–75 (1992).

Sivak, B. et al., "Contact Lens Design for Lateralizing Visual Input," *Neuropsychologia*, 23 (6):801–803 (1985).

Zaidel, E., "A Technique for Presenting Lateralized Visual Input with Prolonged Exposure," *Vision Res.*, 15:283–289 (1975).

Dimond, S.J. et al., "The Use of Contact Lenses for the Lateralisation of Visual Input in Man," *Acta Psychologica* 39:341–349 (1975).

Dimond, S.J. et al., "Differing emotional response from right and left hemispheres," *Nature* 261:690–692 (1976).

*Primary Examiner*—Hung Xuan Dang
*Attorney, Agent, or Firm*—Hamilton, Brook, Smith & Reynolds, P.C.

[57] ABSTRACT

Therapeutic glasses for changing the psychological state of a user and a method for using the glasses are disclosed. The therapeutic glasses include at least one lens of a size sufficient to cover an eye of the user, wherein at least one lens restricts vision to a lateral visual field. The method includes wearing the glasses for a sufficient period of time, thereby stimulating the user to achieve a change in the psychological state of the user.

4 Claims, 2 Drawing Sheets

METHOD FOR USING THERAPEUTIC GLASSES FOR STIMULATING A CHANGE IN THE PSYCHOLOGICAL STATE OF A SUBJECT

BACKGROUND OF THE INVENTION

It has been known since antiquity that the brain is composed of two hemispheres, and people have been attempting for centuries to exploit this fact in explanations of psychological function. By the middle of the 19th century, neurologists had begun to understand that the left hemisphere was dominant for language. In this century, scientists have found the right hemisphere to be dominant for other abilities, such as the understanding and expression of emotion. This partial independence of hemispheres was confirmed in split brain experiments in animals and later in humans showing that hemispheric specialization and partial hemispheric independence could exist together. Research has found that in normal persons the right brain has intelligence and autonomous mental functions separate from those of the left brain.

The right brain and left brain are capable of having their own mentation and actions. Observations have indicated that the cognitive faculties of the right brain in split brain and left-hemispherectomy patients can be fully developed. An isolated right hemisphere has the capacity for autonomous perception, memory, thought, emotion and volition. The right brain, in split-brain patients, can also induce or affect behavior without a correct conscious, left-sided understanding of the reason behind it. In normal individuals, the right hemisphere can have intact mental faculties, separate from and often beyond the awareness of the patient's left-sided mind.

Therefore, a need exists for an apparatus and method that can stimulate a subject by changing the side of the brain which predominates to achieve a change in the psychological state of the subject.

SUMMARY OF THE INVENTION

The present invention is directed to therapeutic glasses for changing the psychological state of a user and is also directed to a method of using the therapeutic glasses.

The therapeutic glasses include at least one lens of a size sufficient to cover an eye of the user, wherein at least one lens sufficiently restricts vision to a lateral visual field to achieve a change in the psychological state of the subject and wherein the lateral visual field can be selectively changed by the user. The lens can be selectively adjusted by the user to change the restriction of vision to a different lateral visual field.

The method includes providing to a user therapeutic glasses having at least one lens of a size sufficient to cover an eye of the subject, wherein at least one lens restricts vision to a lateral field. The therapeutic glasses are worn for a sufficient period of time, thereby stimulating the user to achieve a change in the psychological state of the user.

The present invention has many advantages. The glasses are useful for treating people having psychological symptoms, such as anxiety, depression, post-traumatic stress disorder, compulsions, eating disorders, addictions, attention deficit disorders and psychoses. Further, the invention is useful for helping to relieve stress and to enhance a person state of well-being.

DETAILED DESCRIPTION OF THE INVENTION

The features and details of the method and apparatus of the invention will now be more particularly described with reference to the accompanying drawings and pointed out in the claims. The same numeral present in different figures represents the same item. It will be understood that the particular embodiments of the invention are shown by way of illustration and not as limitations of the invention. The principal features of this invention can be employed in various embodiments without departing from the scope of the invention. All percentages and parts are by weight unless otherwise indicated.

Figure 1:
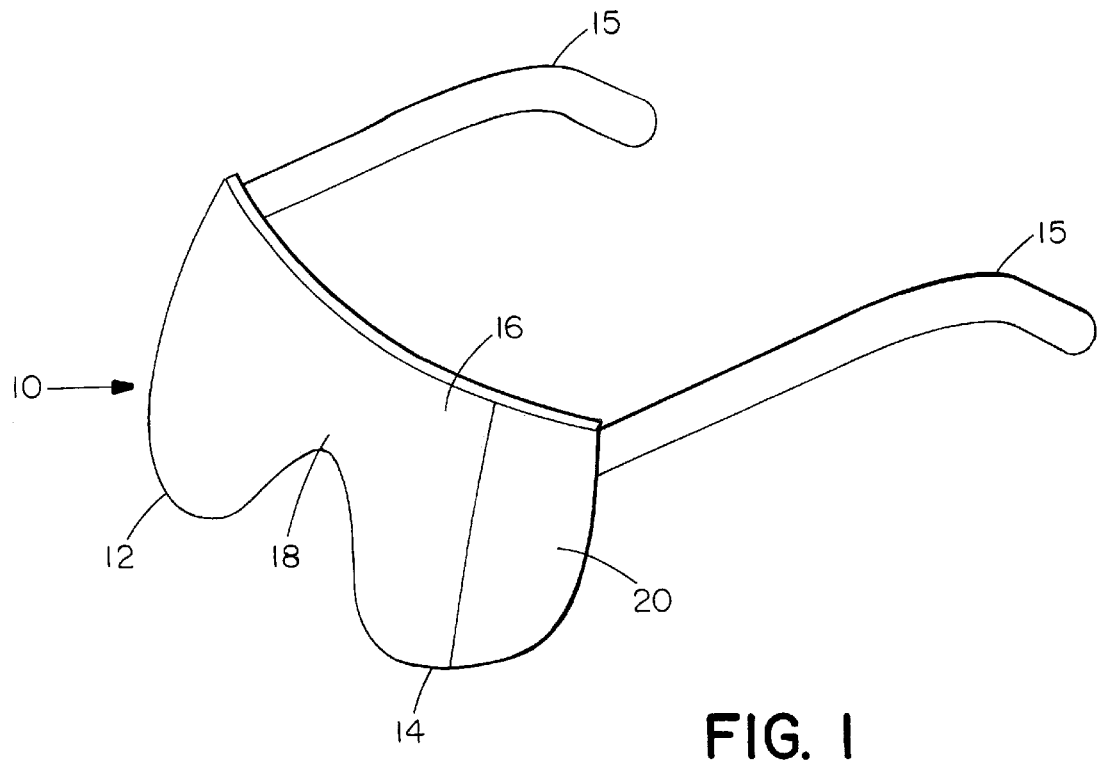
FIG. 1 is a perspective view of one embodiment of the present invention.

This invention relates to therapeutic glasses for changing the psychological state of a user. As shown in FIG. 1, one embodiment of the invention is therapeutic glasses 10 formed from modified safety glasses of a transparent composition, such as polycarbonate or polystyrene, and having first lens 12 and second lens 14. Bows 15 extend sufficiently to pass over the ears of the user. Therapeutic glasses 10 are suitable for covering at least one eye of the wearer. Therapeutic glasses 10 are covered on either the inside or outside surface of first lens 12 and second lens 14 with an essentially opaque substance, such as an adhesive tape, paint or other similar coating that can block the view of the wearer. Alternatively, first lens 12 and second lens 14 can be impregnated with the opaque substance. Typically, first lens 12 (right lens) is fully coated and portion 16 covers about half of second lens 14 (left lens) proximate to bridge 18 of therapeutic glasses 10. Therapeutic glasses 10 are configured to restrict viewing to area 20 of the left half of second lens 14. Covered portion 16 of second lens 14 can have a covered area in the range of between about 50 and 75 percent. In a preferred embodiment, second lens 14 is covered on about sixty percent of the area. Such therapeutic glasses can be worn by a user for a sufficient period of time, thereby stimulating the user to achieve a change in the psychological state of the user.

Figure 2:
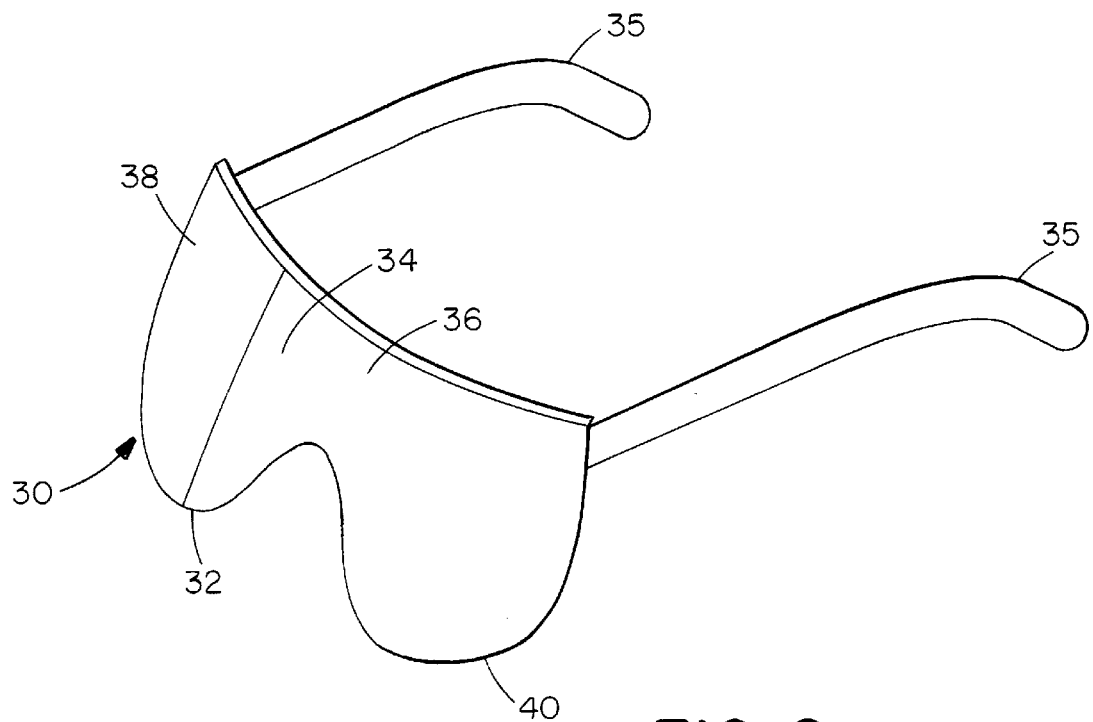
FIG. 2 is a perspective view of a second embodiment of the present invention.

As shown in FIG. 2, second therapeutic glasses 30 are essentially the same as therapeutic glasses 10 shown in FIG. 1. In this embodiment, first lens 32 (right lens) has partially covered area 34 proximate to bridge 36 and transparent area 38 is distal from bridge 36 for limiting vision to the right lateral visual field of the right eye. Bows 35 extend sufficiently to pass over the ears of the user. Second lens 40 (left lens) is sufficiently opaque to block vision.

Figure 3:
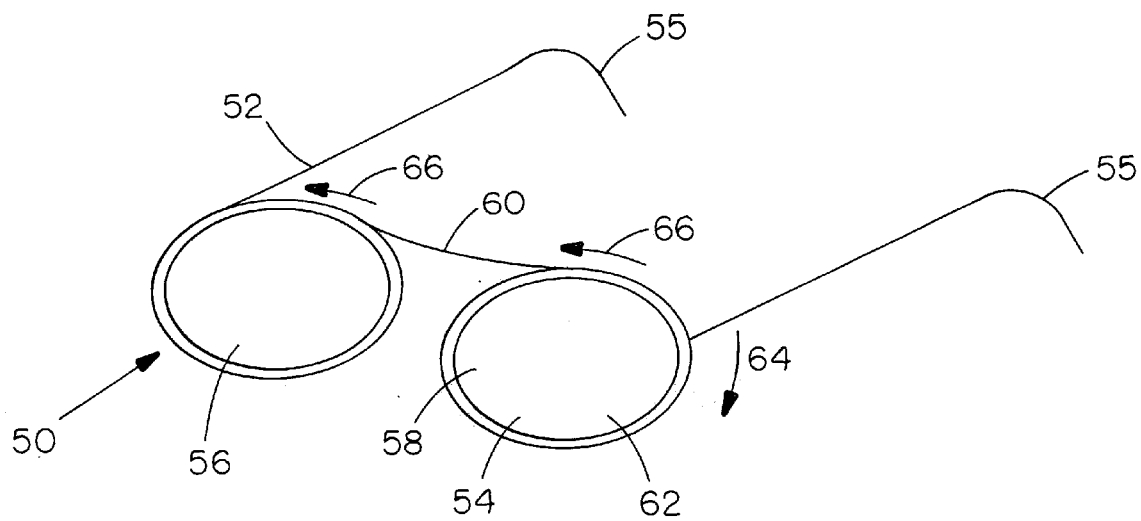
FIG. 3 is a perspective view of a third embodiment of the present invention.

As shown in FIG. 3, another embodiment of the invention includes third therapeutic glasses 50 having frame 52 typically used in eyeglasses and sunglasses. Frame 52 can be formed of a suitable material, such as wire or plastic.

Therapeutic glasses 50 has first lens 54 and second lens 56. First lens 54 can be opaque on first side 58 proximate to bridge 60. Bows 55 extend sufficiently to pass over the ears of the user. Second side 62 can be essentially transparent. The tinting is substantially uniform along the vertical axis of first lens 54 and second lens 56. First lens 54 and second lens 56 can be tinted with various colors, such as blue, red or green. The color blue has been found to be particularly favorable by users. Alternatively, first lens 54 and second lens 56 are essentially opaque or dark on the right side of each and progressively less tinted towards the left side of the lenses where they can be essentially clear. In a preferred embodiment, the outer surfaces of the lenses are coated with a reflective material, such as gold, silver or aluminum, to provide a uniform appearance to a viewer, thereby giving the impression that the wearer is wearing regular sunglasses.

First lens 54 and second lens 56 can be tinted with a photochromic material that allows the tinting to change as a result of lighting conditions. Alternatively, portions of the lenses can be tinted with an electrochromic material, which can be powered by a control unit and battery, to allow the user to change the degree of tinting in the lenses as desired and select the lateral visual field to be restricted. An example of a suitable tinting material and control unit is shown in U.S. Pat. No. 5,264,877, issued to Hussey, the teachings of which are incorporated herein by reference. Therapeutic glasses 50 can have the lenses mounted to frame 52 to allow them to be flipped up in direction 64 in a manner similar to sunglasses worn by baseball players.

First lens 54 and second lens 56 in frame 52 can be mounted in a manner to allow the lenses to be rotated in direction 66 in which the plane the lenses lie. For example, the user may desire to rotate first lens 54 and second lens 56 in order to change the visual field restriction from the left side to the right side, thereby stimulating a different change in the psychological state of a user.

Figure 4:
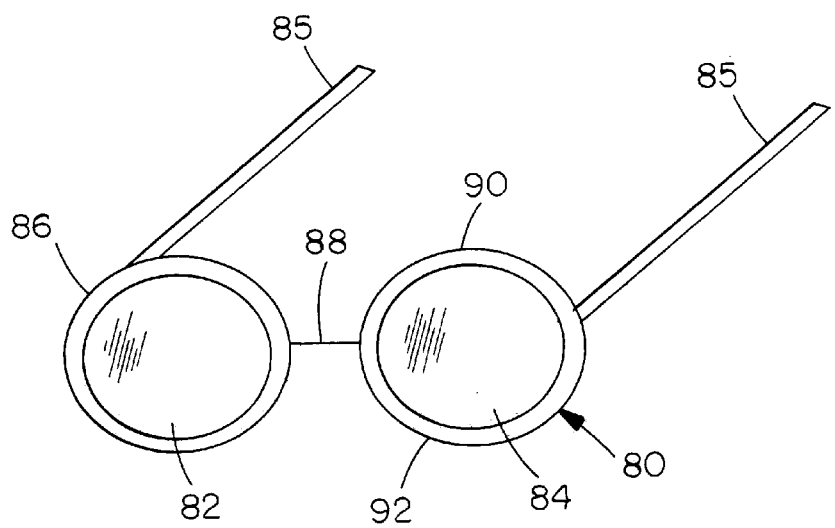
FIG. 4 is a perspective view of a fourth embodiment of the present invention.

As shown in FIG. 4, therapeutic glasses 80 has first lens 82 and second lens 84 in frame 86 which has bridge 88 between the lenses approximately midway between top portion 90 and bottom portion 92 of the glasses. First lens 82 and second lens 84 can have a gradient tint similar to the lenses disclosed in FIG. 3. Bridge 88 is configured to allow therapeutic glasses 80 to be flipped around and worn upside down in order to block the opposite lateral field. For example, therapeutic glasses 80 can have the right side of first lens 82 and second lens 84 sufficiently opaque to restrict vision to the right lateral visual field. Therapeutic glasses 80 can then be flipped around and worn with the left lateral visual field blocked. Bows 85 are sufficiently straight to pass over the ears of the user to allow the user to wear therapeutic glasses 80 in either direction. Bows 85 can be slightly curved in toward the head of the user to help secure the glasses. Depending on the hemisphere the wearer would like to stimulate, therapeutic glasses 80 are worn with the left visual field blocked or the right visual field blocked.

Another embodiment of the invention includes a contact lens having a tint gradient along the horizontal axis from left to right or right to left while having a substantially uniform tint gradient along the vertical axis of the contact lens. The tint gradient along the horizontal axis is preferably linear. The lens sufficiently restricts vision to a lateral visual field to achieve a change in the psychological state of the wearer.

The therapeutic glasses have been found to be beneficial to a patient undergoing psychotherapy. The therapeutic glasses can be worn during psychotherapy sessions with a psychotherapist. In combination with psychotherapy sessions or by themselves, the therapeutic glasses can help reduce symptoms of anxiety, depression or a compulsive disorder, such as an eating disorder, including anorexia nervosa and bulimia. Other compulsive disorders including alcohol abuse and gambling may be helped. Other problems that can be helped include dyslexia, stress-induced heart disease and post-traumatic stress disorder. The therapeutic glasses can be used in counseling and for use in amplifying, diagnosing or describing a psychological problem. The therapeutic glasses are useful for circumstances where one hemisphere of the brain is visually stimulated over the other hemisphere by differentially stimulating the retinas. Such a stimulation can result in electroencephalographic (EEG) activity, indicating a shift in hemispheric dominance.

In psychotherapy a patient can alternate between lateral visual fields and induce both an increase and a decrease in the person's symptoms to show him that his fears reside only in a part of his mind. The embodiments in FIGS. 3 and 4 are designed to facilitate easy switching between the left and right lateral fields. In the embodiment shown in FIG. 3, both lenses can be rotated 180 degrees to change the lateral visual field which is stimulated. In the embodiment shown in FIG. 4, the entire frame can be rotated 180 degrees to change the lateral visual field which is stimulated. With the embodiments shown in FIGS. 1 and 2, the subject can switch between embodiments to alter the lateral visual field which is stimulated. The method allows some patients who have had only a negative view of the world to see the world from a new more optimistic, more mature perspective.

The user does not need to undergo psychotherapy or the like to benefit from using the therapeutic glasses. Many people, who are considered normal and wear the therapeutic glasses, can perceive a reduction in stress and increase in well being. Depending upon the individual and the change in psychological state desired, the user can selectively change the restriction of the visual field to the field that provides the desired result.

The therapeutic glasses are worn at various times, such as during psychotherapy counseling sessions and times of anxiety or at any time the wearer wants to decrease his stress. The therapeutic glasses are worn for a sufficient period of time that can be in the range of between a few minutes and many hours to stimulate the user to achieve a change in the psychological state of the user. For example, the therapeutic glasses can be worn by a passenger on an airplane to help reduce the anxiety of flying. In another embodiment, the therapeutic glasses are worn at home or in the office during a period of anxiety. The therapeutic glasses with translucent material can be worn while walking. However, because the therapeutic glasses with opaque restrict the vision of the user to one visual field while wearing, it is recommended that the glasses be worn while sitting or lying down. Walking with them should only be attempted after much experience while wearing. It is not recommended operating an automobile or heavy machinery while wearing the therapeutic glasses with opaque material.

Although not wanting to be limited to a theory why the therapeutic glasses are effective in treating numerous problems and disorders, it is believed that certain changes in the psychological state of a person can be changed by stimulating one hemisphere of the brain separately from the other hemisphere. Whether it is the left or right hemisphere which dominates can often markedly affect a person's personality and some of the psychological systems he might have. By restricting vision to a portion of the retina of an eye that is connected to a particular hemisphere of the brain, that hemisphere can be stimulated preferentially. The eyes are connected to the brain so that vision to the left side of a person goes first to the opposite (right) hemisphere and vision to the right side of a person goes first to the left hemisphere.

It is believed that humans can have two autonomous minds, one associated with the left brain and one with the right brain and that there is a human relationship between human left and right minds, and the issues which apply to any relationship apply to the one within us. For example, in some people the left minds "dominate" and "suppress" their right minds. In others, the right mind can dominate. Symptoms can be produced if a trouble side dominates the personality. For example, some of these right dominant people are called "neurotic", because they express emotions or engage in behaviors that are difficult to understand and often seem irrational. Of course, some peoples' minds live in harmony with mutual respect and cooperation.

To test the efficacy of the therapeutic glasses, seventy out-patient psychotherapy patients were asked to participate. All gave written, informed consent, and each participated without remuneration. The patients ranged in age from 18 to 73 with a mean of 43 (sd=10.8). There were 39 males. Eleven patients were left-handed and 59 were right-handed by the Edinburgh Handedness criteria. The primary, current DSM-IV diagnoses by structural clinical research interviews fell into six groups: 1) dysthymic disorder (N=20); 2) anxiety disorders (N=7); 3) major depression (N=21); 4) schizophrenia (N=2); 5) bipolar I disorder (N=2); and 6) post-traumatic stress disorder (PTSD) (N=18). Thirty-seven were taking psychotropic medications, most commonly serotonin reuptake inhibitors or benzodiazepins or both. Thirty-three had not taken medications for at least two weeks prior to the study.

Two pairs of therapeutic glasses, as shown in FIGS. 1 and 2, were constructed, each made by covering safety glasses with a white adhesive tape over one side and about sixty percent of the medial aspect of the other side. Each pair of therapeutic glasses was taped so that it permitted vision to only either the left visual field or the right visual field. Patients were free to move their eyes, head or body, but were encouraged to look out of the exposed area so that about half of their visual field on that side was obstructed.

Following objective questions about their level of anxiety in the different conditions, 42 patients were engaged, who found at least a one point difference on a five-point anxiety scale (none, mild, moderate, quite-a-bit or extreme) between lateral visual fields, in an unstructured interview while they wore the therapeutic glasses a second time, shortly after the first. On repeat trials, as part of a pilot study, seven additional patients responded to the therapeutic glasses and were also interviewed with the glasses on.

Of these 49 patients who experienced at least a one-point difference in anxiety between sides, the mean age was 42.9 (sd=9.8). There were 24 females and 39 right-handed patients. Twenty-seven were taking psychotropic medications.

Three of these responsive patients were tested in a follow-up session in which their EEG's were monitored during two baseline periods, as well as while they wore, in randomized order, the experimental therapeutic glasses and two comparison goggles. The comparison goggles were constructed so that either the left or right side was completely taped, and the other side was taped only over the bottom fourth of the lens. These comparison goggles allowed for monocular vision which a number of studies have demonstrated can activate the contralateral hemisphere. The bottom one fourth of the unoccluded side of the comparison goggles was taped to give them a more complex appearance in an attempt to disguise that they were being used as a control. At least ninety seconds of EEG tracings were recorded in each condition with electrodes placed in a standard 10/20 system. The electrodes were referenced to linked mastoids and all impedances were less than five ohms. After artifact removal, an asymmetry index (L−R/L+R) was calculated from the means of the frontal and temporal leads on the left (F1, F3, F7, T3, T5) and right (F2, F4, F8, T4, T6) sides for both the theta and the alpha power spectrums. The asymmetry indices for the two pairs of therapeutic glasses were compared as were those for the comparison goggles and the two baseline recordings.

By Pearson chi-square tests, there were no significant differences between the 49 responders and the 21 non-responders, who were not interviewed, on the basis of diagnosis, sex, medication or handedness, although handedness approached significance (chi-square=2.717, df=1,68) p=0.099 because 91% left handers were responders.

Forty of the 49 patients interviewed reported feeling more regressed and symptomatic on one side and more mature and less symptomatic on the other. These patients usually reported being surprised by their experience. Twenty-six patients later consistently used the therapeutic glasses in their ongoing psychotherapy, and all of these patients found their use in therapy sessions to be of value.

All three patients tested with EEG monitoring manifested changes in their laterality indices with the two pairs of therapeutic glasses in the expected direction. That is, for each, the asymmetry index (L−R/L+R) derived from the mean frontal and temporal leads for theta activity was greater with the left vision field therapeutic glasses than with the right vision field therapeutic glasses (mean difference=−0.023 $\mu v$, sd=0.025). In these patients, the lateralized differences were greater with the therapeutic glasses than with the comparison goggles (mean difference=−0.0144, sd=0.039) or with the repeated baseline conditions (mean difference=0.0076, sd=0.030). For these three patients, none of these differences were statistically significant by the Wilcoxon Rank-Sum Test.

A test was conducted to determine whether lateral visual field stimulation could alter EEG activity and affect in a laboratory setting. A comparison was conducted of EEG and anxiety level changes induced by two pairs of experimental goggles, each taped over one lens entirely and over the middle 60% of the other side, and by two pairs of comparison goggles. The experimental goggles restricted vision to the left visual field (LVF) or right visual field (RVF); the comparison goggles, to the left or right eye. Eleven subjects, ten right-handed, seven male, included three patients with PTSD and eight asymptomatic college students. The theta and alpha EEG activity in the mean of frontal and temporal leads was compared. All leads were referred to linked mastoids. Ninety seconds of EEG's were recorded in each condition and after artifact removal. A laterality index (LI), which equals (L−R)/(L+R), for each pair of randomly presented goggles was calculated.

With the experimental goggles the mean laterality index for the eleven subjects was less with the RVF than the LVF. The RVF-LVF difference in LI was −0.109, sd=0.19, (Wilcoxon Signed-Rank=−26.00, p=0.019) for theta, and −0.033, sd=0.054 for alpha (Signed-Rank=−21.00, p=0.067). For the comparison goggles, the R−L difference in LI was −0.033, sd=0.08 for theta (Signed-Rank=−9, p=0.25) and 0.002, sd=0.078 for alpha (Signed-Rank=0.00, p=1). The absolute differences in anxiety levels (rated on a 5 point scale) between experimental goggles were significantly greater than those between comparison goggles by Wilcoxon Signed-Rank test, Signed-Rank=10.5, p=0.031. Thus, restricting vision to lateral visual fields appeared to activate the contralateral hemisphere and to change anxiety levels from those of the other lateral field.

Equivalents

Those skilled in the art will recognize or be able to ascertain using no more than routine experimentation, many equivalents to the specific embodiments of the invention described specifically herein. Such equivalents are intended to be encompassed in the scope of the claims.

I claim:

1. A method for stimulating a change in the psychological state of a subject, comprising the steps of:

a) providing first therapeutic glasses having two lenses, wherein each are of a size sufficient to cover the eyes of a subject and both lenses restrict vision to a first lateral field;

b) wearing said first therapeutic glasses for a sufficient period of time to allow lateral visual field stimulation;

c) assessing the lateral visual field stimulation of the first lateral field for a change in the psychological state of the subject;

d) providing second therapeutic glasses having two lenses, wherein each are of a size sufficient to cover the eyes of a subject and both lenses restrict vision to a second lateral field, which is different from the first lateral visual field;

e) wearing said therapeutic glasses for a sufficient period of time to allow lateral visual field stimulation;

f) assessing the lateral visual field stimulation of the second lateral field for a change in the psychological state of the subject;

g) comparing the lateral visual field stimulation of the first lateral field and the second lateral visual field stimulation of the second lateral field to determine the more favorable change in psychological state; and h) wearing the therapeutic glass with vision restricted to the lateral visual field that provides the more favorable change in the psychological state of the subject.

2. The method of claim 1 wherein the change in the psychological state of the subject includes a change of psychological symptoms displayed by the subject.

3. The method of claim 1 wherein the change in the psychological state of the subject includes a change in the well-being of the subject.

4. The method of claim 1 wherein one of the eyes has both lateral visual fields blocked.

* * * * *